United States Patent [19]

Bloch et al.

[11] 3,998,896
[45] Dec. 21, 1976

[54] PRODUCTION OF MONOCHLORO-SUBSTITUTED SATURATED COMPOUNDS

[75] Inventors: Herman S. Bloch, Skokie; Louis Schmerling, Riverside, both of Ill.

[73] Assignee: UOP Inc., Des Plaines, Ill.

[22] Filed: Aug. 22, 1975

[21] Appl. No.: 607,083

Related U.S. Application Data

[63] Continuation-in-part of Ser. No. 507,086, Sept. 18, 1974, abandoned.

[52] U.S. Cl. .................. 260/658 C; 260/658 R; 260/659 R
[51] Int. Cl.² ............................................. C07C 17/00
[58] Field of Search ....... 260/658 R, 658 C, 648 R, 260/651 R, 659 R

[56] References Cited

UNITED STATES PATENTS 2,562,369  7/1951  Schmerling .................. 260/648 R

*Primary Examiner*—Allen B. Curtis
*Assistant Examiner*—Thomas A. Waltz
*Attorney, Agent, or Firm*—James R. Hoatson, Jr.; Kimbley L. Muller; William H. Page, II

[57] ABSTRACT

Monochloro-substituted saturated compounds are prepared by condensing an aliphatic saturated hydrocarbon containing a secondary of tertiary carbon atom with a monochloromonoolefin possessing up to 14 carbon atoms and having the chlorine atom attached to one of the doubly-bonded carbon atoms in the presence of a free radical-generating catalyst.

9 Claims, No Drawings

PRODUCTION OF MONOCHLORO-SUBSTITUTED SATURATED COMPOUNDS

CLOSELY RELATED APPLICATIONS

This is a continuation-in-part of our previously filed application Ser. No. 507,086 filed Sept. 18, 1974, now abandoned, all the teachings of which are specifically incorporated herein by reference.

This invention relates to a process for the production of monochloro-substituted compounds. More specifically, this invention relates to a process for the preparation of monochloro-substituted saturated compounds which comprises condensing an aliphatic saturated hydrocarbon containing a secondary or tertiary carbon atom with a monochloromonoolefin possessing up to 14 carbon atoms and having the chlorine atom attached to one of the doubly-bonded carbon atoms in the presence of a free radical-generating catalyst.

The free radical-induced reaction of a saturated hydrocarbon with an unsaturated hydrocarbon is well known in the prior art. It is also well known in the art that a saturated hydrocarbon may be condensed by means of free radical-generators with a chloroolefin characterized by the presence of at least one chlorine atom on each of the doubly-bonded carbon atoms.

In contradistinction to the prior art it has now been discovered that an aliphatic saturated hydrocarbon containing a secondary or tertiary carbon atom may be condensed with a monochloromonoolefin possessing up to 14 carbon atoms and having the chlorine atom attached to only one of the doubly-bonded carbon atoms to produce a monochloro-substituted saturated compound, said condensation being effected in the presence of a free radical-generating catalyst. The condensation reaction may also be enhanced by the presence of a promoter composition of matter comprising a hydrogen chloride compound such as aqueous hydrochloric acid or anhydrous hydrogen chloride. The promoter composition of matter will enable a greater percentage conversion of the original reactants, namely, the aliphatic saturated hydrocarbon and the monochloromonoolefin and an increase of percent yield of the monochloro-substituted saturated compound.

The desired products of the process of this invention namely, monochloro-substituted saturated compounds are utilized in the chemical industry in many ways. For example, the heavier molecular weight monochloro-substituted saturated compounds may be converted to alcohols for futher use in the preparation of detergents. Likewise, they may be used as organic solvents or in the preparation of various special alkyl aromatic compounds by alkylation of aromatics with the monochloro-substituted saturated compounds.

It is therefore an object of this invention to provide a process for the preparation of monochloro-substituted saturated compounds.

A further object of this invention is to provide a process for the preparation of monochloro-substituted saturated compounds utilizing a certain promoter composition of matter comprising hydrogen chloride compounds which permit a more economic batch and continuous type process.

In one aspect an embodiment of this invention resides in a process for producing a monochloro-substituted saturated compound which comprises condensing an aliphatic saturated hydrocarbon containing a secondary or tertiary carbon atom with a monochloromonoolefin possessing up to 14 carbon atoms and having the chlorine attached to one of the doubly-bonded carbon atoms in the presence of a free radical-generating catalyst at reaction conditions and recovering the resultant monochloro-substituted saturated compound.

In another aspect an embodiment of this invention resides in a process for the preparation of monochloro-substituted substituted saturated compounds which comprises condensing an aliphatic saturated hydrocarbon containing a secondary or tertiary carbon atom with a monochloromonoolefin processing up to 14 carbon atoms and having the chlorine atom attached to one of the doubly-bonded carbon atoms in the presence of a free radical-generating catalyst and a hydrogen chloride promoter composition of matter at reaction conditions, and recovering the resultant monochloro-substituted saturated compound.

A specific embodiment of this invention resides in a process for preparing 1-chloro-3,3-dimethylpentane which comprises condensing isopentane with vinyl chloride at a temperature of 140° C. in the presence of a catalyst comprising di-t-butyl peroxide and recovering the resultant 1-chloro-3,3-dimethylpentane.

Another specific embodiment of this invention resides in a process for preparing 2-(2-chlorocyclopentyl)propane which comprises condensing propane with 1-chlorocyclopentene-1 at a temperature of 140° C. in the presence of a catalyst comprising di-t-butyl peroxide and a promoter composition of matter comprising hydrogen chloride in an anhydrous state and recovering the resultant 2-(2-chlorocyclopentyl) propane.

Other objects and embodiments of the hereinbefore set forth invention will be described in the following further detailed description of the present invention.

As hereinbefore set forth, the present invention is concerned with a process for preparing monochloro-substituted saturated compounds which comprises condensing an aliphatic saturated compound containing a secondary or tertiary carbon atom with a monochloromonoolefin possessing up to 14 carbon atoms and having the chlorine atom attached to the doubly-bonded carbon atom in the presence of a free radical-generating catalyst. The reaction is effected under conditions which include an elevated temperature at least as high as the initial decomposition temperature of the free radical-generating catalyst. In addition, another reaction condition involves pressure, said pressure ranging from atmospheric to about 100 atmospheres or more. When superatmospheric pressures are employed, said pressures are afforded by the introduction of vaporized reactants or a substantially inert gas such as nitrogen into the reaction zone. Another variable which is employed is the ratio of reactants, the aliphatic saturated hydrocarbon containing a secondary or tertiary carbon atom usually being present in a mole ratio of from about 1:1 up to about 10:1 mols per mol of the monochloromonoolefin in which the chlorine atom is attached to one of the doubly-bonded carbon atoms.

Examples of suitable aliphatic saturated hydrocarbons containing a secondary or tertiary carbon atom will include in particular, all aliphatic saturated hydrocarbons possessing from about 3 to about 40 carbon atoms such as propane, n-butane, n-pentane, n-hexane, n-heptane, n-octane, n-nonane, n-decane, n-undecane, n-dodecae, n-tridecane, n-tetradecane, n-pentadecane, n-hexadecane, n-heptadecane, n-octadecane, n-nonadecane, n-eicosane, n-heneicosane, n-docosane, n- tricosane, n-tetracosane, n-pentacosane, n-hexacosane, n-heptacosane, n-octacosane, n-nonacosane, and n-triacontane, isobutane, isopentane, methylpentanes, methylhexanes, methylheptanes, methyloctanes, etc., methylnonanes, methyldecanes, methylundecanes, methyldodecanes, methyltridecanes methyltetradecanes, methylpentadecanes methylhexadecanes, methylheptadecanes, methyloctadecanes, methylnonadecanes, methyleicosanes methylheneicosanes, methyltricosanes, methyltetracosanes, methylpentacosanes, methylhexacosanes, methylheptacosanes, methyloctacosanes, methylnonacosanes and methyltriacontanes, 2,3-dimethylbutane, neohexane, 2,3-dimethylpentane, 2,3-dimethylhexane, 2,4-dimethylpentane, 3,4-diethyloctane, 3,4-diethylnonane, 4,5-dipropyltetradecane, 7,8-dihexyleicosane, 3-methyl-4-ethyl-6-propyltricosane, 3-methyl-7-octyltricosane, 4,5-dihexylheptacosane, 5-propyltetradecane, 6-propylundecane, 5,6-diethyldecane, 7,8-dihexylpentacosane, 3,3-dimethyl-4-ethyl-6,6-dipentylheptadecane, etc.

Suitable monochloromonoolefins which may be condensed with the aforementioned aliphatic saturated hydrocarbons containing a secondary or tertiary carbon atom will include monochloromonoolefins in which the chlorine atom is attached to one of the doubly-bonded carbon atoms, including aliphatic and cyclic olefins. Such monochloromonoolefins include vinyl chloride, in particular, and 1-chloropropene-1, 2-chloropropene-1, 1-chlorobutene-1, 2-chlorobutene-1, 1-chloropentene-1, 1-chlorohexene-1, 2-chlorohexene1, 3-chlorohexene-3, 1-chloroheptene-1, 2-chloroheptene-1, 3-chloroheptene-3, 4-chloroheptene-3, 1-chlorooctene-1, 1-chlorononene-1, 1-chlorodecene-1, 1-chloroundecene-1, 2-chlorodecene 2, 3-chlorodecene-3, 1- chlorododecene-1, 1-chlorotridecene-1, 1-chlorotetradecene-1, 7-chlorotetradecene-7, 2-methyl-1-chlorobutene-1, 3,5,6- trimethyl-1-chloroheptene-1, 1-chlorocyclopentene-1, 1-chloro-2-methylcyclopenetene-1, 1-chlorocyclohexene-1, 1-chlorocycloheptene-1, 1-chlorocyclooctene-1, etc.

The catalytic compositions of matter which are used in the process of the present invention comprise organic peroxides which are designated as free radical-generating catalysts. Examples of these catalysts which may be used include, in particular, the disubstituted hydrogen peroxides such as di-t-butyl peroxide, t-butyl perbenzoate, benzoyl peroxide, etc. It is also contemplated within the scope of this invention that hydroperoxides such as acetyl hydroperoxide and t-butyl hydroperoxide may also be used although not necessarily with equivalent results.

The particular catalytic composition of matter chosen in the process of the present invention has an effect upon reaction temperature in that the reaction temperatures should be at least as high as the initial decomposition temperature of the free radical-generating catalysts, such as the peroxide compound, in order to liberate and form free radicals which promote the reaction. In selecting the particular reaction temperature for use in the process of the present invention two considerations must be taken into account. First, sufficient energy by means of heat must be supplied to the reaction system so that reactants, namely, the saturated aliphatic hydrocarbon containing a secondary or tertiary carbon atom and the monochloromonoolefin in which the chlorine is attached to one of the doubly-bonded carbon atoms, will be activated sufficiently for condensation to take place when free radicals are generated by the catalyst. Second, free radical-generating catalysts such as the peroxy compounds, particularly organic peroxides, decompose at a measurable rate with time in a logarithmic function dependent upon temperature. The rate of decomposition can be, and ordinarily is, expressed as the half life of the peroxide at a particular temperature. For example, the half-life in hours of di-t-butyl peroxide is 17.5 hours at 125° C., 5.3 hours at 135° C., and 1.7 hours at 145° C. (calculated from data for the first 33% decomposition). A reaction system temperature can be selected so that the free radical generating catalyst decomposes smoothly with the generation of free radicals at a half-life which is not too long. In other words, sufficient free radicals must be present to induce the present chain reaction to take place, and these radicals must be formed at a temperature at which the reactants are in a suitably activated state for condensation. When the half-life of the free radical-generating catalyst is greater than 10 hours, radicals are not generated at a sufficient rate to cause a reaction of the process of the present invention to go forward at a practical rate. Thus, the reaction temperature may be within the range of from about 50° C. to about 300° C. and at least as high as the decomposition temperature of the catalyst, by which is meant a temperature such that the half-life of the free radical-generating catalyst is not greater than 10 hours. Since the half-life for each free radical-generating catalyst is different at different temperatures, the exact temperature to be utilized in a particular reaction will vary. However, persons skilled in the art are well acquainted with the half-life versus the temperature data for different free-radical-generating catalysts. Thus it is within the skill of one familiar with the art to select a particular temperature needed for any particular catalyst. However, the operating temperatures generally do not exceed the decomposition temperature of the catalyst by more than about 150° C. since free radical-generating catalysts decompose rapidly under such conditions. For example, when a free radical-generating catalyst such as t-butyl perbenzoate is used having a decomposition temperature of approximately 115° C. the process is run at a temperature ranging from 115° C. to about 265° C. When di-t-butyl peroxide having a decomposition temperature of about 130° C. is used, the process is run at a temperature ranging from 130° to about 280° C. Higher reaction temperatures may be employed, but little advantage is gained if the temperature is more than the hereinbefore mentioned 150° C. higher than the decomposition temperature of the catalyst. The general effect of increasing the operating temperature is to accelerate the rate of condensation reaction between the monochloromonoolefin in which the chlorine atom is attached to one of the doubly-bonded carbon atoms and the saturated aliphatic hydrocarbon containing a secondary or tertiary carbon atom. However, the increased rate of reaction may be accompanied by a certain amount of undesired side reactions such as polymerization of the monochloromonoolefins.

It is contemplated within the scope of the present invention that a promoter comprising a hydrogen chloride compound will enhance the quantity of the monochloro-substituted saturated compound produced in the reaction. By "hydrogen chloride compound" is meant either anhydrous hydrogen chloride or aqueous hydrochloric acid. The effect upon the mechanism of the hereinbefore set forth reaction is that of increasing the yield of the monochloro-substituted product. The mechanism of the action of the hydrogen chloride (which exhibits a marked and unique effect on free-radical induced reactions) is shown by the following example:

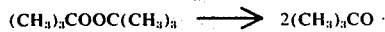

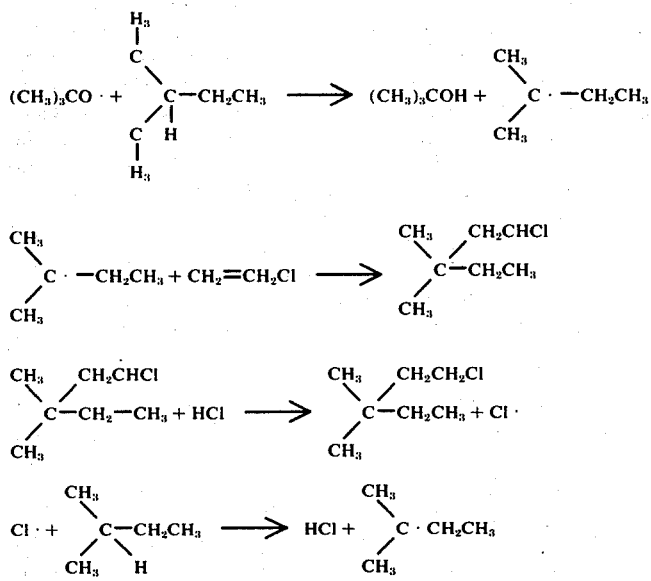

The so-formed t-pentyl radical starts a new cycle and the 1-chloro-3,3-dimethylpentane is produced by the resulting chain reaction.

In the absence of hydrogen chloride, the following chain reaction occurs:

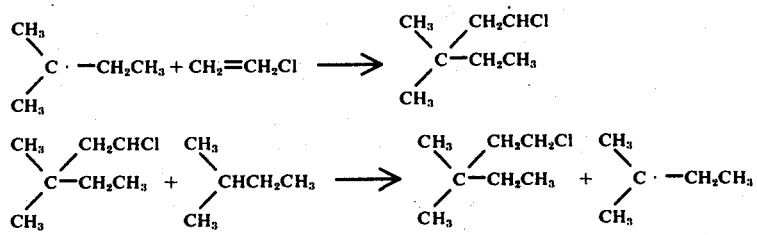

The chlorodimethylpentyl radical abstracts a hydrogen atom more rapidly from hydrogen chloride than from isopentane and therefore the 1-chloro-3,3-dimethylpentane is formed more rapidly (and hence in higher yield) than in the absence of hydrogen chloride. The desired compound is then formed before the monochloromonoolefin or the chlorodimethylpentyl radical undergo polymerization or other side reactions.

It is understood that the aforementioned aliphatic saturated hydrocarbons containing a secondary or tertiary carbon atom, monochloromonoolefins in which the chlorine atom is attached to one of the doubly-bonded carbon atoms, and free radical-generating catalysts, are only representative of the classes of compounds which may be employed and that the present invention is not necessarily limited thereto.

The process of this invention may be effected in any suitable manner and may comprise either a batch or a continuous operation. For example, when a batch type operation is employed, the reactants comprising the aliphatic saturated hydrocarbon containing a secondary or tertiary carbon atom and the monochloromonoolefin in which the chlorine atom is attached to one of the doubly-bonded carbon atoms are placed in an appropriate apparatus along with a free radical generating catalyst which may have a promoter comprising a hydrogen chloride compound added thereto. If atmospheric pressure is to be employed, the reaction vessel is then heated to a predetermined operating temperature. After maintaining the reactants in the reaction vessel at this temperature (suitably under reflux conditions) for a period of time which may range from 0.5 up to about 30 hours or more in duration, the heating is discontinued and the vessel allowed to return to room temperature. The reaction mixture is then recovered, separated from the catalyst and the promoter and subjected to conventional means of purification and separation, said means including washing, drying, extraction, evaporation, fractional distillation, etc., whereby the desired monochloro-substituted saturated compound is recovered. Alternatively, if superatmospheric pressures are to be employed in the reaction, the reactants are charged to a pressure vessel such as a rotating autoclave, which contains a free radical-generating catalyst and a promoter comprising a hydrogen chloride compound if it is desired in the reaction. The autoclave is sealed and a substantially inert gas such as nitrogen or helium is pressed in until the desired operating pressure is reached. The autoclave is then heated to the desired operating temperature and maintained thereat for a predertermined residence time. At the end of this time heating is discontinued, the autoclave is allowed to return to room temperature and the excess pressure is discharged. The autoclave is opened and the reaction mixture is then treated in a manner similar to that hereinbefore set forth whereby the desired monochloro-substituted saturated compounds are recovered from the autoclave.

It is also contemplated within the scope of this invention that the reaction process for obtaining a monochloro-substituted saturated compound may be effected in a continuous manner of operation. When such a type of process is employed, the reactants comprising the aliphatic saturated hydrocarbon containing a secondary or tertiary carbon atom and the monochloromonoolefin in which the chlorine atom is attached to one of the doubly-bonded carbon atoms are continuously charged to the reaction vessel under conditions of good mixing as are the free radical-generating catalyst and the promoter comprising hydrogen chloride compounds, if used; the reactants and the catalyst and the promoter may be added from the same or from different inlet lines. After completion of the desired residence time, the reactor effluent is continually withdrawn and subjected to a conventional means of separation whereby the desired monochloro-substituted saturated compounds are recovered, while any unreacted starting material comprising the aliphatic saturated hydrocarbon or the monochloromonoolefin are recycled to the reaction zone to form a portion of the feedstock.

Examples of monochloro-substituted saturated compounds which may be prepared according to the process of this invention will include 1-chloro-3,3-dimethylbutane, 1-chloro-3,3-dimethylpentane, 4-chloro-2,2dimethylhexane, 2-chloro-1-cyclopentylpropane, 1-chloro-2,3-dimethyloctane, 2-(2-chlorocyclopentyl)-butane, 1chloro-3-methylhexane, 1-chloro-3-methyl-3-ethylpentane, 3-chloro-5-pentyltetradecane, etc.

It is to be further understood that the aforementioned monochloro-substituted saturated compounds are only representative of the class of compounds which may be prepared and that the present invention is not necessarily limited thereto.

The following examples which are given to illustrate the process of the present invention are not, likewise, intended to limit the generally broad scope of the present invention in strict accordance therewith.

EXAMPLE I

In this example 104.0 grams of isopentane, 17.0 grams of vinyl chloride, 21.0 grams of concentrated hydrochloric acid, 17.0 grams of water and 6.0 grams of di-t-butyl peroxide were charged to a glass-lined 850 ml rotating autoclave. The autoclave was heated to a temperature of 130° to 140° C. under an initial pressure of 30 atmospheres of nitrogen for a period of time comprising 4 hours. After the 4-hour period of time, the resultant product was removed from the autoclave and analyzed by means of gas-liquid chromatography instrumentation, mass spectrometry and infrared spectroscopy instrumentation. The analysis disclosed a 26 mol percent yield of 1-chloro-3,3-dimethylpentane and a 7 mol percent yield of byproduct comprising 1-chloro-5, 5-dimethyl-2-heptene, produced from the reaction of two mols of vinyl chloride with the isopentane and loss of hydrogen chloride.

EXAMPLE II

In this example 100.0 grams of n-heptane, 31.0 grams of vinyl chloride, 20.0 grams of concentrated hydrochloric acid, 20.0 grams of water and 6.0 grams of di-t-butyl peroxide were charged to a glass-lined 850 ml rotating autoclave. The autoclave was heated to a temperature of 130° C. to 140° under an initial pressure of 30 atmospheres of nitrogen for a period of time comprising 4 hours. After the 4-hour period of time, the resultant product was removed from the autoclave and analyzed by means of gas-liquid chromatography instrumentation, mass spectrometry and infrared spectroscopy instrumentation. The analysis disclosed the major monochloro-substituted saturated compound to be 2-(2-chloroethyl)heptane (also known as 1-chloro-3-methyloctane).

EXAMPLE III

In this example propane and 1-chlorocyclopentene-1 are added to an 850 ml rotating autoclave which contains di-t-butyl peroxide and concentrated anhydrous hydrochloric acid. The autoclave is heated to a temperature of 140° C. and maintained at this temperature for a period of time comprising 4 hours. At the end of this period of time the product is removed from the autoclave, separated and analyzed by means of gas-liquid chromatography and infrared spectroscopy, said analyses disclosing the resultant monochloro-substituted saturated compounds to include 2-(2-chlorocyclopentyl)propane.

EXAMPLE IV

In this example 1-chlorotetradecene-1 and isopentane are added to an 850 ml rotating autoclave which contains t-butyl perbenzoate and anhydrous hydrogen chloride. The autoclave is heated to a temperature of 250° C. and maintained thereat for a period of time comprising 4 hours. At the end of this period of time, the product is removed from the autoclave and analyzed by means of gas-liquid chromatography instrumentation, mass spectrometry and infrared spectroscopy instrumentation, aid analyses disclosing the resultant monochloro-substituted saturated compounds to comprise 4-chloromethyl-3,3-dimethylhexadecane.

EXAMPLE V

In this example vinyl chloride and 3-methylpentane are added to an 850 ml rotating autoclave which contains t-butyl hydroperoxide and aqueous hydrochloric acid. The autoclave is heated to a temperature of 150° C. and maintained thereat for a period of time comprising 2 hours. At the end of this period of time, the product is removed from the autoclave, separated and analyzed by means of gas-liquid chromatography and infrared spectroscopy, said analyses disclosing the resultant monochloro-substituted saturated compounds to include 1-chloro-3-methyl-3-ethylpentane.

We claim as our invention:
1. In a process for producing a monochloro-substituted saturated compound by condensing an acyclic aliphatic saturated hydrocarbon containing a secondary or tertiary carbon atom with a monochloromonoolefin possessing up to 14 carbon atoms and having the chlorine atom attached to one of the doubly-bonded carbon atoms in the presence of a free radical-generating peroxide catalyst at a temperature at least as high as the decomposition temperature of the free radical catalyst and a pressure of from about 1 atmosphere to about 100 atmospheres, and recovering the resultant monochloro-substituted saturated compound, the improvement which comprises effecting said condensation in the presence of a promoter comprising hydrogen chloride.

2. The process of claim 1 further characterized in that the peroxy catalyst is di-t-butyl peroxide.

3. The process of claim 1 further characterized in that hydrogen chloride is anhydrous.

4. The process of claim 1 further characterized in that the hydrogen chloride is aqueous.

5. The process of claim 1 further characterized in that the aliphatic saturated hydrocarbon is isopentane, the monochloromonoolefin is vinyl chloride and the monochloro substituted saturated compound is 1-chloro-3,3-dimethylpentane.

6. The process of claim 1 further characterized in that the aliphatic saturated hydrocarbon is propane, the monochloromonoolefin is 1-chlorocyclopentene-1 and the monochloro-substituted saturated compound is 2-(2-chlorocyclopentyl)propane.

7. The process of claim 1 further characterized in that the aliphatic saturated hydrocarbon is heptane, the monochloromonoolefin is vinyl chloride and the monochloro substituted saturated compound is 2-(2-chloroethyl)heptane.

8. The process of claim 1 further characterized in that the aliphatic saturated hydrocarbon is isopentane, the monochloromonoolefin is 1-chlorotetradecene-1 and the monochloro-substituted saturated compound is 4-chloromethyl-3,3-dimethylhexadecane.

9. The process of claim 1 further characterized in that the aliphatic saturated hydrocarbon is 3-methylpentane, the monochloromonoolefin is vinyl chloride and the monochloro substituted saturated compound is 1-chloro-3-methyl-3-ethyl-pentane.

* * * * *